United States Patent
Matsuda

(10) Patent No.: US 9,012,509 B2
(45) Date of Patent: *Apr. 21, 2015

(54) METHOD OF TREATING NON-ALCOHOLIC STEATOHEPATITIS

(71) Applicant: MediciNova, Inc., La Jolla, CA (US)

(72) Inventor: Kazuko Matsuda, Beverly Hills, CA (US)

(73) Assignee: MedicNova, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/152,846

(22) Filed: Jan. 10, 2014

(65) Prior Publication Data

US 2014/0128473 A1    May 8, 2014

Related U.S. Application Data

(63) Continuation of application No. 13/706,161, filed on Dec. 5, 2012.

(60) Provisional application No. 61/568,517, filed on Dec. 8, 2011.

(51) Int. Cl.
*A01N 37/10* (2006.01)
*A61K 31/19* (2006.01)
*A61K 31/192* (2006.01)

(52) U.S. Cl.
CPC .................................. *A61K 31/192* (2013.01)

(58) Field of Classification Search
None
See application file for complete search history.

(56) References Cited

U.S. PATENT DOCUMENTS

| | | | |
|---|---|---|---|
| 4,788,055 A | 11/1988 | Fischer et al. | |
| 4,816,055 A | 3/1989 | Reunamaki et al. | |
| 4,816,264 A | 3/1989 | Phillips et al. | |
| 4,828,836 A | 5/1989 | Elger et al. | |
| 4,834,965 A | 5/1989 | Martani et al. | |
| 4,834,985 A | 5/1989 | Elger et al. | |
| 4,985,585 A | 1/1991 | Ohashi | |
| 4,996,047 A | 2/1991 | Kelleher et al. | |
| 5,071,646 A | 12/1991 | Malkowska | |
| 5,133,974 A | 7/1992 | Paradissis | |
| 5,290,812 A | 3/1994 | Ohashi et al. | |
| 7,060,854 B2 | 6/2006 | Locke et al. | |
| 7,064,146 B2 | 6/2006 | Locke et al. | |
| 7,728,169 B2 * | 6/2010 | Locke et al. | ............... 562/431 |

OTHER PUBLICATIONS

Gonzalez-Periz (Resolution of Adipose Tissue Inflammation, The Scientific World Journal, 2010, 10, 832-856).*
Gonzalez-Periz et al., Resolution of Adipose Tissue Inflammation, The Scientific World Journal, 2009, 10, 832-856.
Hirata, et al., "Effect of Telmisartan or Losartan for treatment of nonalcoholic fatty liver disease: Fatty liver protection trial by Telmisartan or losartan study (FANTASY)", International Journal of Endocrinology, pp. 1-10, (2013).
Shaner et al. in Pesticide Biotrasformation in Plants and Microorganisms (Hall, J. et al.) ACS Symposium Series, American Chemical Society; Wash. DC, 2000 (p. 356 2nd paragraph).
US Office Action on 069803-3401 DTD Jun. 20, 2013.

* cited by examiner

Primary Examiner — Dennis Heyer
Assistant Examiner — Daniel M Podgorski
(74) Attorney, Agent, or Firm — Gilberto M. Villacorta; Photon Rao; Foley & Lardner LLP

(57) ABSTRACT

A compound of Formula (I):

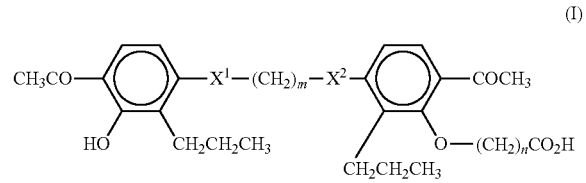

or a metabolite thereof, or an ester of the compound of Formula (I) or the metabolite thereof, or a pharmaceutically acceptable salt of each thereof, wherein m, n, $X^1$ and $X^2$ are as defined herein, is useful for treating non-alcoholic steatohepatitis (NASH) and/or reducing one or more of hepatic fibrosis, lobular inflammation, and hepatocellular ballooning.

30 Claims, No Drawings

METHOD OF TREATING NON-ALCOHOLIC STEATOHEPATITIS

CROSS-REFERENCE TO RELATED PATENT APPLICATIONS

This application claims the benefit of the priority date of U.S. application Ser. No. 13/706,161 filed Dec. 5, 2012, which claims the benefit of priority date of Provisional U.S. Application No. 61/568,517, filed Dec. 8, 2011, the contents of each of which are incorporated by reference herein in their entirety.

FIELD OF THE INVENTION

This invention relates to methods of treating non-alcoholic fatty liver disease (NAFLD), and/or non-alcoholic steatohepatitis (NASH), and/or negative effects of each thereof by administering phenoxyalkylcarboxylic acids such as MN-001 and MN-002.

BACKGROUND OF THE INVENTION

Non-alcoholic fatty liver disease (NAFLD) refers to fat accumulation in the liver that is not related to alcohol consumption. Fat may accumulate as a result of obesity, diabetes or other conditions. In a small number of people, NAFLD progresses to liver inflammation, scarring and, eventually, liver failure. This serious form of the disease is sometimes called non-alcoholic steatohepatitis (NASH). NAFLD and NASH are a growing problem worldwide, affecting people of every age. NAFLD and NASH are currently the fastest-rising indicator for liver transplant.

SUMMARY OF THE INVENTION

In one aspect, the present invention provides a method of treating a patient suffering from non-alcoholic fatty liver disease (NAFLD) or non-alcoholic steatohepatitis (NASH) comprising administering to a patient in need thereof an effective amount of a compound of Formula (I):

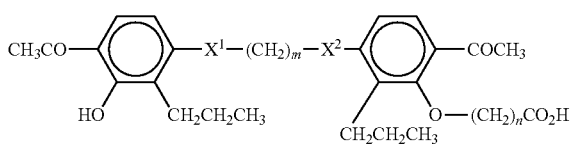

or a metabolite thereof, or an ester of the compound of Formula (I) or the metabolite thereof, or a pharmaceutically acceptable salt of each thereof, wherein m is an integer from 2 to 5, and n is an integer from 3 to 8, $X^1$ and $X^2$ each independently represent a sulfur atom, a oxygen atom, a sulfinyl (—S(O)—) group or a sulfonyl (—S(O)$_2$—) group, provided that $X^1$ and $X^2$ are not simultaneously oxygen atoms.

In another aspect, the present invention provides a method of reducing liver inflammation in a patient suffering from NAFLD or NASH comprising administering to a patient in need thereof an effective amount of a compound of Formula (I), or an ester thereof, or a pharmaceutically acceptable salt of each thereof, wherein the compound of Formula (I) is defined as above.

In a preferred embodiment, the compound of Formula (I) is a compound of Formula (IA) (or MN-001):

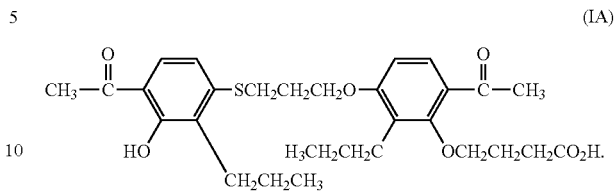

In another preferred embodiment, the metabolite of the compound of Formula (I) and (IA) is a compound of Formula (IB) (or MN-002):

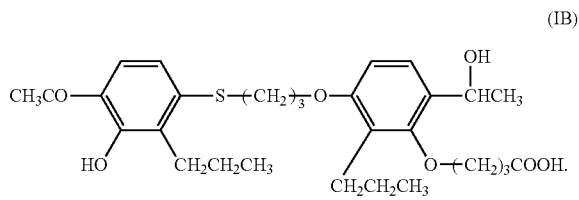

In one embodiment, the patient is suffering from NAFLD. In another embodiment, the patient is suffering from NASH.

DETAILED DESCRIPTION OF THE INVENTION

Definitions

As used herein, and in the appended claims, the singular forms "a," "an" and "the" include plural references unless the context clearly dictates otherwise.

"Administering" or "Administration of" a drug to a patient (and grammatical equivalents of this phrase) includes both direct administration, including self-administration, and indirect administration, including the act of prescribing a drug. For example, as used herein, a physician who instructs a patient to self-administer a drug and/or provides a patient with a prescription for a drug is administering the drug to the patient.

"Cx" when placed before a group refers to the number of carbon atoms in that group to be X.

"Alkyl" refers to a monovalent acyclic hydrocarbyl radical having 1-12 carbon atoms. Non limiting examples of alkyl include methyl, ethyl, propyl, isopropyl, butyl, isobutyl, tertiary butyl, pentyl, hexyl and the like.

"Aryl" refers to a monovalent aromatic hydrocarbyl radical having up to 10 carbon atoms. Non-limiting examples of aryl include phenyl and naphthyl.

"Heteroaryl" refers to an aromatic group of from 1 to 10 carbon atoms and 1 to 4 heteroatoms selected from the group consisting of oxygen, nitrogen, sulfur within the aromatic ring, wherein the nitrogen and/or sulfur atom(s) of the heteroaryl are optionally oxidized (e.g., N-oxide, —S(O)— or —S(O)$_2$—). Such heteroaryl groups can have a single ring (e.g., pyridyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. Non limiting examples of heteroaryl include pyridyl, pyrrolyl, indolyl, thiophenyl, and furyl.

"Cycloalkyl" refers to a monovalent non-aromatic cyclic hydrocarbyl radical having 3-12 carbon atoms. Non limiting examples of cycloalkyl include cyclopropyl, cyclobutyl, cyclopentyl, cyclohexyl, and the like.

"Heterocyclyl" refers to a monovalent non-aromatic cyclic group of 1 to 10 carbon atoms and 1 to 4 heteroatoms selected from the group consisting of oxygen, nitrogen, sulfur within the cycle, wherein the nitrogen and/or sulfur atom(s) of the heteroaryl are optionally oxidized (e.g., N-oxide, —S(O)— or —S(O)$_2$—). Such heteroaryl groups can have a single ring (e.g., piperidinyl or tetrahydrofuranyl) or multiple condensed rings wherein the condensed rings may or may not be aromatic and/or contain a heteroatom provided that the point of attachment is through an atom of the non-aromatic heterocyclyl group. Non limiting examples of heterocyclyl include pyrrolidinyl, piperidinyl, piperazinyl, and the like.

"Amino" refers to —NH$_2$.

"Alkylamino" refers to —NHR$_B$, wherein R$_B$ is C$_1$-C$_6$ alkyl optionally substituted with 1-3 aryl, heteroaryl, cycloalkyl, or heterocyclyl group.

"Dialkylamino" refers to —N(R$_B$)$_2$, wherein R$_B$ is defined as above.

"Comprising" shall mean that the methods and compositions include the recited elements, but not exclude others. "Consisting essentially of" when used to define methods and compositions, shall mean excluding other elements of any essential significance to the combination for the stated purpose. Thus, a composition consisting essentially of the elements as defined herein would not exclude trace contaminants from the isolation and purification method and pharmaceutically acceptable carriers, such as phosphate buffered saline, preservatives and the like. "Consisting of" shall mean excluding more than trace elements of other ingredients and substantial method steps for administering the compositions of this invention or process steps to produce a composition or achieve an intended result. Embodiments defined by each of these transitional terms and phrases are within the scope of this invention.

"Effective amount" of a compound utilized herein is an amount that, when administered to a patient with NAFLD or NASH will have the intended therapeutic effect, e.g., alleviation, amelioration, palliation or elimination of one or more manifestations of the medical condition in the patient. The full therapeutic effect does not necessarily occur by administration of one dose (or dosage), and may occur only after administration of a series of doses. Thus, an effective amount may be administered in one or more administrations.

"Non-alcoholic steatohepatitis" or NASH is a common liver disease, which resembles alcoholic liver disease, but occurs in people who drink little or no alcohol. The major feature in NASH is fat in the liver, along with inflammation and damage. NASH can lead to cirrhosis, in which the liver is permanently damaged and scarred and is no longer able to work properly. NASH affects 2 to 5 percent of the U.S. population. Currently, no specific therapies for NASH exist. An additional 10 to 20 percent of Americans have fat in their liver, but no substantial inflammation or liver damage, a condition called "non-alcoholic fatty liver disease" (NAFLD). Although having fat in the liver is not normal, by itself it probably causes little harm or permanent damage. If fat is suspected based on blood test results or scans of the liver, this problem is referred to as NAFLD. If a liver biopsy is performed in this case, it will show that some people have NASH while others have NAFLD.

NASH is usually first suspected in a person who is found to have elevations in liver tests that are included in routine blood test panels, such as alanine aminotransferase (ALT) or aspartate aminotransferase (AST). When further evaluation shows no apparent reason for liver disease (such as medications, viral hepatitis, or excessive use of alcohol) and when x rays or imaging studies of the liver show fat, NASH is suspected. NASH is diagnosed and separated from NAFLD by a liver biopsy. For a liver biopsy, a needle is inserted through the skin to remove a small piece of the liver. NASH is diagnosed when examination of the tissue with a microscope shows fat along with inflammation and damage to liver cells. If the tissue shows fat without inflammation and damage, NAFLD is diagnosed. An important piece of information learned from the biopsy is whether scar tissue has developed in the liver.

NASH can slowly worsen, causing scarring or fibrosis to appear and accumulate in the liver. As fibrosis worsens, cirrhosis develops; the liver becomes severely scarred, hardened, and unable to function normally. Once serious scarring or cirrhosis is present, few treatments can halt the progression. A person with cirrhosis experiences fluid retention, muscle wasting, bleeding from the intestines, and liver failure. Liver transplantation is the only treatment for advanced cirrhosis with liver failure, and transplantation is increasingly performed in people with NASH. For example, NASH ranks as one of the major causes of cirrhosis in the U.S.A., behind hepatitis C and alcoholic liver disease.

"Pharmaceutically acceptable" refers to non-toxic and suitable for administration to a patient, including a human patient.

"Pharmaceutically acceptable salts" refer to salts that are non-toxic and are suitable for administration to patients. Non-limiting examples include alkali metal, alkaline earth metal, and various primary, secondary, and tertiary ammonium salts. When the ester of the compound of Formula (I) includes a cationic portion, for example, when the ester includes an amino acid ester, the salts thereof can include various carboxylic acid, sulfonic acid, and miner acid salts. Certain non limiting examples of salts include sodium, potassium, and calcium salts.

"Protecting groups" refer to well known functional groups which, when bound to a functional group, render the resulting protected functional group inert to the reaction to be conducted on other portions of a compound and the corresponding reaction condition, and which can be reacted to regenerate the original functionality under deprotection conditions. The protecting group is selected to be compatible with the remainder of the molecule. A "carboxylic acid protecting group" protects the carboxylic functionality of the phenoxyalkylcarboxylic acids during their synthesis. Non limiting examples of carboxylic acid protecting groups include, benzyl, p-methoxybenzyl, p-nitrobenzyl, allyl, benzhydryl, and trityl. Additional examples of carboxylic acid protecting groups are found in standard reference works such as Greene and Wuts, Protective Groups in Organic Synthesis., 2d Ed., 1991, John Wiley & Sons, and McOmie Protective Groups in Organic Chemistry, 1975, Plenum Press. Methods for protecting and deprotecting the carboxylic acids disclosed herein can be found in the art, and specifically in Greene and Wuts, supra, and the references cited therein.

"Treating" a medical condition or a patient refers to taking steps to obtain beneficial or desired results, including clinical results. For purposes of the various aspects and embodiments of the present invention, beneficial or desired clinical results include, but are not limited to, reduction, alleviation, or amelioration of one or more manifestations of or negative effects of NAFLD and/or NASH, improvement in one or more clinical outcomes, diminishment of extent of disease, delay or slowing of disease progression, amelioration, palliation, or stabilization of the disease state, and other beneficial results described herein.

Preferred Embodiments

In one aspect, the present invention provides a method of treating a patient suffering from non-alcoholic fatty liver disease (NAFLD) or non-alcoholic steatohepatitis (NASH) comprising administering to a patient in need thereof an effective amount of a compound of Formula (I):

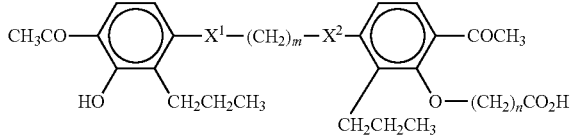

(I)

or a metabolite thereof, or an ester of the compound of Formula (I) or the metabolite thereof, or a pharmaceutically acceptable salt of each thereof, wherein m is an integer from 2 to 5, and n is an integer from 3 to 8, $X^1$ and $X^2$ each independently represent a sulfur atom, an oxygen atom, a sulfinyl group or a sulfonyl group, provided that $X^1$ and $X^2$ are not simultaneously oxygen atom.

In another aspect, the present invention provides a method of reducing liver inflammation in a patient suffering from NAFLD or NASH comprising administering to a patient in need thereof an effective amount of a compound of Formula (I), or a metabolite thereof, or an ester of the compound of Formula (I) or the metabolite thereof, or a pharmaceutically acceptable salt of each thereof, wherein the compound of Formula (I) is defined as above.

As used herein, "a metabolite thereof" refers to a metabolite that shows substantially similar therapeutic activity as a compound of Formula (I). Non limiting examples of such metabolites include compounds where the —COCH₃ group, of a compound of Formula (I), that is attached to the phenyl containing the —O—(CH₂)ₙCO₂H moiety is metabolized to a 1-hydroxyethyl (—CH(OH)Me) group.

Metabolites containing such a 1-hydroxyethyl group contain an asymmetric center on the 1-position of the 1-hydroxyethyl group. The corresponding enantiomers and mixtures thereof, including racemic mixtures, are included within the metabolites of the compound of Formula (I) as utilized herein.

As used herein, "an ester thereof" refers to an ester of the phenolic hydroxy group and/or an ester of the carboxylic acid shown in the compound of Formula (I), and an ester of the 1-hydroxyethyl (an aliphatic hydroxy group) group of a metabolite of the compound Formula (I). An ester of the phenolic and/or the aliphatic hydroxy groups can include, without limitation, as the corresponding acid, a carboxylic acid $R_4$—CO₂H, wherein $R_4$ is $C_1$-$C_6$ alkyl, aryl, heteroaryl, $C_3$-$C_{12}$ cycloalkyl, or $C_2$-$C_8$ heterocyclyl, wherein the alkyl, aryl, heteroaryl, cycloalkyl, or heterocyclyl are optionally substituted with 1-4 $C_1$-$C_3$ alkyl, aryl, CO₂H, amino, alkylamino, or dialkylamino groups. Other acids such as mono-, di-, or tri phosphoric acids are also contemplated. An ester of the carboxylic acid can include, without limitation, as the corresponding alcohol, a compound of formula $R_4$—OH, wherein $R_4$ is defined as above. In one embodiment, only the carboxylic acid in Formula (I) is esterified. In another embodiment, only the phenolic hydroxy group in Formula (I) is esterified. In another embodiment, $R_4$ is $C_1$-$C_4$ alkyl. As will be apparent to the skilled artisan, such esters act as prodrugs that are hydrolyzed in vivo to release the compound of Formula (I) or a salt thereof.

In a preferred embodiment, the compound of Formula (I) is a compound of Formula (IA):

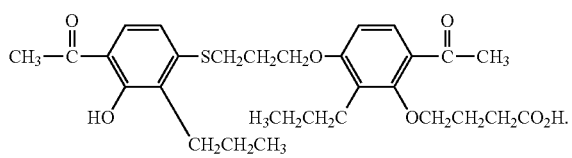

(IA)

In another preferred embodiment, the metabolite of the compound of Formula (I) and (IA) is a compound of Formula (IB):

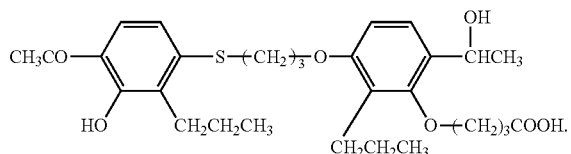

(IB)

In one embodiment, the patient is suffering from NAFLD. In another embodiment, the patient is suffering from NASH. In another embodiment, the compound is administered orally. In another embodiment, the compound is administered as a tablet or a capsule. In another embodiment, the compound of Formula (IA) is present in polymorphic form A that is substantially free of other polymorphic forms. In another embodiment, the compound is administered as a liquid dosage form. In another embodiment, the compound is administered in an amount from 100 to 4,000 mg/day, divided into one, two, or three portions.

Without being bound by theory, the compounds utilized herein are effective in treating NAFLD and/or NASH due in part to their anti-inflammatory activity. It is believed that various receptor sites can be blocked by the compounds utilized in herein. Few, if any, of the known inhibitors of inflammatory disease embody all of the following sites of activity in a single molecule: inhibition of 1) leukotriene synthesis, 2) leukotriene D-4 receptors, 3) leukotriene E-4 receptors, 4) cAMP PDE III, 5) cAMP PDE IV, 6) synthesis of thromboxaneA-2, 7) eosinophil migration and 8) 20 lymphocyte migration. The above mechanisms are involved and cooperate in different degrees and with different specificities among the wide variety of cells interacting in the so-called "inflammatory cascade," to produce a fission-like result. By blocking a wide variety of action sites, the compounds utilized herein are contemplated to be effective for treating NAFLD and/or NASH.

Synthesis

The synthesis and certain biological activity of the compounds of Formula (I) are described in U.S. Pat. No. 4,985,585 which is incorporated herein in its entirety by reference.

For example, the compound of Formula (IA) is prepared by reacting a phenol of Formula (II):

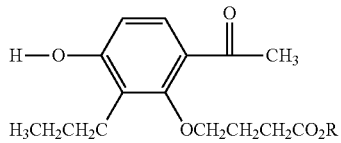

wherein, R is a carboxylic acid protecting group, with a compound of Formula (III):

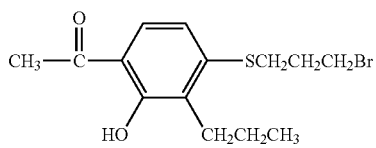

to provide a compound of Formula (IC):

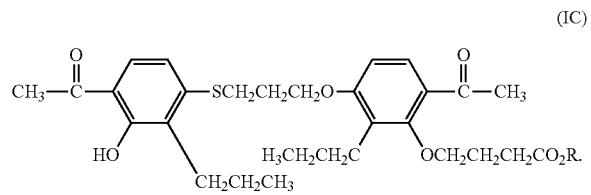

Non limiting examples of acid protecting groups, or R groups, include $C_1$-$C_6$ alkyl, benzyl, benzhydryl, and trityl, wherein the benzyl, benzhydryl, or trityl group is optionally substituted with 1-6 $C_1$-$C_6$ alkyl, halo, and/or $C_1$-$C_6$ alkoxy groups. It will be apparent to the skilled artisan that a leaving group other than the bromo group of Formula (III) may be used. Non limiting examples of such other leaving groups include chloro or tosylate.

Deprotection of the protected carboxylic acid of Formula (IC) provides the compound of Formula (IA). As is apparent based on this disclosure, compounds of Formula (IC) are in some embodiments useful in accordance with this invention. Non-limiting examples of deprotection methods include, alkaline hydrolysis and hydrogenolysis under $H_2$ and a catalyst such as Pd/C or Pt/C.

The reactions are carried out in an inert organic solvent, for example and without limitation, acetone, methylethylketone, diethylketone, or dimethylformamide. The nucleophilic displacement reaction may be conducted at a temperature below room temperature up to the reflux temperature of the solvent, in the presence of an inorganic base, such as potassium carbonate or sodium carbonate, and optionally in the presence of potassium iodide. The reactions are carried out for a period of time sufficient to provide substantial product as determined by well known methods such as thin layer chromatography and $^1$H-NMR. Other compounds utilized herein are made by following the procedures described herein and upon appropriate substitution of starting materials, and/or following methods well known to the skilled artisan. See also, U.S. Pat. No. 5,290,812 (incorporated herein in its entirety by reference).

The compound of Formula (IA) is recrystallized under controlled conditions to provide an essentially pure orthorhombic polymorph, referred to as Form A crystals (e.g., 90% or more, preferably at least 95% Form A). Polymorphic Form A and processes for producing it are described in U.S. Pat. Nos. 7,060,854 and 7,064,146; which are incorporated herein in their entirety by reference. All polymorphic forms of the compound of Formula (I) are active, but polymorphic Form A is preferred. Under certain conditions, the solubility and the bioavailability of this polymorph is superior to the other polymorphs and thus Form A may offer improved solid formulations.

Form A crystals can be obtained, for example, by dissolving the compound of Formula (IA) in 5 to 10 parts by weight of ethanol at 25-40° C. to give a yellow to orange solution. The ethanol solution is charged with 1-10 parts of water and agitated at 20-25° C. for about 15-60 minutes and then at 5-10° C. for an additional period of 1-4 hours, preferably 2.0-3.0 hours, resulting in an off-white suspension. To this suspension is added 5-15 parts of water and the mixture is agitated at 5-10° C. for an additional 1-4 hours, preferably 1.5-2.0 hours. A solid, white to off-white product is isolated by vacuum filtration and the filter cake is washed with water and dried in a vacuum at 25-40° C. for 12-24 hours.

For compounds utilized herein that exist in enantiomeric forms, such as certain metabolites of the compound of Formula (I) (for example, the compound of formula IB), the two enantiomers can be optically resolved. Such a resolution is performed, for example, and without limitation, by forming diastereomeric salt of a base such as (S)-(−)-1-(1-naphthyl) ethylamine with the corresponding carboxylic acid compound, or by separating the enantiomers using chiral column chromatography. Intermediates to such compounds, which intermediates also exist in enantiomeric forms can be similarly resolved.

Administration and Formulation

The compounds utilized herein can be administered orally, or by intravenous, intramuscular, and subcutaneous injection, or transdermal methods. Effective dosage levels can vary widely, e.g., from about 100 to 4000 mg per day. In one embodiment, the daily dosage range is 250 to 2,000 mg, given in one, two or three portions. In another embodiment, the dosage is 1000 mg twice a day. In other embodiments, suitable dosages include 1000 mg qd, 1000 mg bid, and 750 mg tid.

Actual amounts will depend on the circumstances of the patient being treated. As those skilled in the art recognize, many factors that modify the action of the active substance will be taken into account by the treating physician such as the age, body weight, sex, diet and condition of the patient, the time of administration, the rate and route of administration. Optimal dosages for a given set of conditions can be ascertained by those skilled in the art using conventional dosage determination tests.

The compounds utilized herein can be formulated in any pharmaceutically acceptable form, including liquids, powders, creams, emulsions, pills, troches, suppositories, suspensions, solutions, and the like. Therapeutic compositions containing the compounds utilized herein will ordinarily be formulated with one or more pharmaceutically acceptable ingredients in accordance with known and established practice. In general, tablets are formed utilizing a carrier such as modified starch, alone or in combination with 10% by weight of carboxymethyl cellulose (Avicel). The formulations are compressed at from 1,000 to 3,000 pounds pressure in the tablet forming process. The tablets preferably exhibit an average hardness of about 1.5 to 8.0 kp/cm$^2$, preferably 5.0 to 7.5 kp/cm$^2$. Disintegration time varies from about 30 seconds to about 15 or 20 minutes.

Formulations for oral use can be provided as hard gelatin capsules wherein the therapeutically active compounds utilized herein are mixed with an inert solid diluent such as calcium carbonate, calcium phosphate or kaolin, or as soft gelatin capsules in which the compounds are mixed with an oleaginous medium, e.g., liquid paraffin or olive oil. Suitable carriers include magnesium carbonate, magnesium stearate, talc, sugar, lactose, pectin, dextrin, starch, gelatin, tragacanth, methylcellulose, sodium carboxymethyl cellulose, a low melting wax, cocoa butter, and the like.

The compounds utilized herein can be formulated as aqueous suspensions in admixture with pharmaceutically acceptable excipients such as suspending agents, e.g., sodium carboxymethyl cellulose, methylcellulose, hydroxypropylmethyl cellulose, sodium alginate, polyvinylpyrrolidone, gum tragacanth and gum acacia; dispersing or wetting agents such as naturally occurring phosphatide, e.g., lecithin, or condensation products of an alkaline oxide with fatty acids, e.g., polyoxyethylene stearate, or condensation products of ethylene oxide with long chain aliphatic alcohols, e.g., heptadecaethylene-oxycetanol, or condensation products of ethylene oxide with partial esters derived from fatty acids and a hexitol, e.g., polyoxyethylene sorbitol monooleate or condensation products of ethylene oxide with partial esters derived from fatty acids and hexitol anhydrides, e.g., polyoxyethylene sorbitan monoleate. Such aqueous suspensions can also contain one or more preservatives, e.g., ethyl- or -n-propyl-p-hydroxy benzoate, one or more coloring agents, one or more flavoring agents and one or more sweetening agents, such as glycerol, sorbitol, sucrose, saccharin or sodium or calcium cyclamate.

Suitable formulations also include sustained release dosage forms, such as those described in U.S. Pat. Nos. 4,788,055; 4,816,264; 4,828,836; 4,834,965; 4,834,985; 4,996,047; 5,071,646; and, 5,133,974, the contents of which are incorporated herein in their entirety by reference.

Other forms suitable for oral administration include liquid form preparations including emulsions, syrups, elixirs, aqueous solutions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizing, and thickening agents. Solid form preparations may contain, in addition to the active component, colorants, flavors, stabilizers, buffers, artificial and natural sweeteners, dispersants, thickeners, solubilizing agents, and the like.

The compounds utilized herein may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example as solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds utilized herein may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds utilized herein may be formulated for administration as suppositories. In such a formulation, a low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds utilized herein may be formulated for vaginal administration. Pessaries, tampons, creams, gels, pastes, foams or sprays containing in addition to the active ingredient such carriers as are known in the art to be appropriate.

The compounds utilized herein may be formulated for nasal administration. The solutions or suspensions are applied directly to the nasal cavity by conventional means, for example, with a dropper, pipette or spray. The formulations may be provided in a single or multidose form. The patient can administer an appropriate, predetermined volume of the solution or suspension via a dropper or pipette. A spray may be administered for example by means of a metering atomizing spray pump.

The compounds utilized herein may be formulated for aerosol administration, particularly to the respiratory tract and including intranasal administration. The compound will generally have a small particle size for example of the order of 5 microns or less. Such a particle size may be obtained by means known in the art, for example by micronization. The active ingredient is provided in a pressurized pack with a suitable propellant such as a chlorofluorocarbon (CFC), (for example, dichlorodifluoromethane, trichlorofluoromethane, or dichlorotetrafluoroethane), carbon dioxide or other suitable gases. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine. The powder carrier will form a gel in the nasal cavity. The powder composition may be presented in unit dose form for example in capsules or cartridges of, for example gelatin or blister packs from which the powder may be administered by means of an inhaler.

When desired, formulations can be prepared with enteric coatings adapted for sustained or controlled release administration of the active ingredient. A common type of controlled release formulation that may be used for the purposes of the present invention comprises an inert core, such as a sugar sphere, a first layer, coated with an inner drug-containing second layer, and an outer membrane or third layer controlling drug release from the inner layer.

The cores are preferably of a water-soluble or swellable material, and may be any such material that is conventionally used as cores or any other pharmaceutically acceptable water-soluble or water-swellable material made into beads or pellets. The cores may be spheres of materials such as sucrose/starch (Sugar Spheres NF), sucrose crystals, or extruded and dried spheres typically comprised of excipients such as microcrystalline cellulose and lactose.

The substantially water-insoluble material in the first layer is generally a "GI insoluble" or "GI partially insoluble" film forming polymer (dispersed or dissolved in a solvent). As examples may be mentioned ethyl cellulose, cellulose acetate, cellulose acetate butyrate, polymethacrylates such as ethyl acrylate/methyl methacrylate copolymer (Eudragit NE-30-D) and ammonio methacrylate copolymer types A and B (Eudragit RL30D and RS30D), and silicone elastomers. Usually, a plasticizer is used together with the polymer. Exemplary plasticizers include: dibutylsebacate, propylene glycol, triethylcitrate, tributylcitrate, castor oil, acetylated monoglycerides, acetyl triethylcitrate, acetyl butylcitrate, diethyl phthalate, dibutyl phthalate, triacetin, fractionated coconut oil (medium-chain triglycerides).

The second layer containing the active ingredient may be comprised of the active ingredient (drug) with or without a polymer as a binder. The binder, when used, is usually hydrophilic but may be water-soluble or water-insoluble. Exemplary polymers to be used in the second layer containing the active drug are hydrophilic polymers such as polyvinylpyrrolidone, polyalkylene glycol such as polyethylene glycol, gelatine, polyvinyl alcohol, starch and derivatives thereof, cellulose derivatives, such as hydroxypropylmethyl cellulose (HPMC), hydroxypropyl cellulose, carboxymethyl cellulose, methyl cellulose, ethyl cellulose, hydroxyethyl cellulose, carboxyethyl cellulose, carboxymethyl hydroxyethyl cellulose, acrylic acid polymers, polymethacrylates, or any other pharmaceutically acceptable polymer. The ratio of drug to hydrophilic polymer in the second layer is usually in the range of from 1:100 to 100:1 (w/w).

Suitable polymers for use in the third layer, or membrane, for controlling the drug release may be selected from water insoluble polymers or polymers with pH-dependent solubility, such as, for example, ethyl cellulose, hydroxypropylmethyl cellulose phthalate, cellulose acetate phthalate, cellulose acetate trimellitate, polymethacrylates, or mixtures thereof, optionally combined with plasticizers, such as those mentioned above.

Optionally, the controlled release layer comprises, in addition to the polymers above, another substance(s) with different solubility characteristics, to adjust the permeability, and thereby the release rate, of the controlled release layer. Exemplary polymers that may be used as a modifier together with, for example, ethyl cellulose include: HPMC, hydroxyethyl cellulose, hydroxypropyl cellulose, methylcellulose, carboxymethylcellulose, polyethylene glycol, polyvinylpyrrolidone (PVP), polyvinyl alcohol, polymers with pH-dependent solubility, such as cellulose acetate phthalate or ammonio methacrylate copolymer and methacrylic acid copolymer, or mixtures thereof. Additives such as sucrose, lactose and pharmaceutical grade surfactants may also be included in the controlled release layer, if desired.

Also provided herein are unit dosage forms of the formulations. In such forms, the formulation is subdivided into unit dosages containing appropriate quantities of the active component (e.g., and without limitation, a compound of Formula (I) or an ester thereof, or a salt of each thereof). The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in Remington: The Science and Practice of Pharmacy 1995, edited by E. W. Martin, Mack Publishing Company, 19th edition, Easton, Pa.

EXAMPLES

Example 1

Treatment of Non-Alcoholic Steatohepatitis (NASH)

250 adults with nonalcoholic steatohepatitis are randomly assigned to receive MN-001 or MN-002, each at a daily dose of 500 mg, or placebo, for up to 6 months. The primary outcome is an improvement in histologic features of nonalcoholic steatohepatitis, as assessed with the use of a composite of standardized scores for steatosis, lobular inflammation, hepatocellular ballooning, and/or fibrosis. The results are analyzed following methods well known to the skilled artisan.

Example 2

Treatment of Non-Alcoholic Fatty Liver Disease (NAFLD)

A randomized, double-blind, placebo-controlled study is performed on 50 patients with NAFLD diagnosed by ultrasound (US) and confirmed by liver biopsy (40 patients). The patients are randomized to receive MN-001 or MN-002 (each at a daily dose of 500 mg for up to 6 months) or placebo. All patients participate in an identical behavioral weight loss program. All patients undergo monthly evaluation by abdominal US. Liver enzyme levels, lipid profiles, insulin levels, and anthropometric parameters are also monitored, and all patients undergo nutritional follow-up evaluation. Patients also undergo a second liver biopsy examination at the end of the study. Serum alanine transaminase levels and steatosis by US are measured as non-limiting endpoints. The results are analyzed following methods well known to the skilled artisan.

The invention claimed is:
1. A method of treating a patient suffering from non-alcoholic steatohepatitis (NASH) comprising administering to a patient in need thereof an effective amount of a compound of Formula (I):

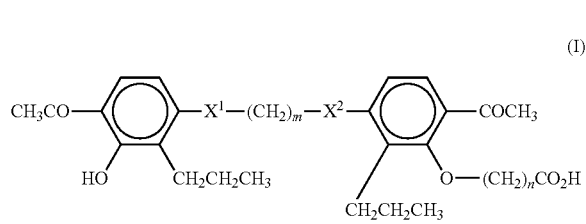

or an ester thereof, or a pharmaceutically acceptable salt of each thereof, wherein m is an integer from 2 to 5, and n is an integer from 3 to 8, $X^1$ and $X^2$ each independently represent a sulfur atom, oxygen atom, sulfinyl group or a sulfonyl group, provided that $X^1$ and $X^2$ are not simultaneously oxygen atom.

2. The method of claim 1, in which the compound of Formula (I) is of Formula (IA)

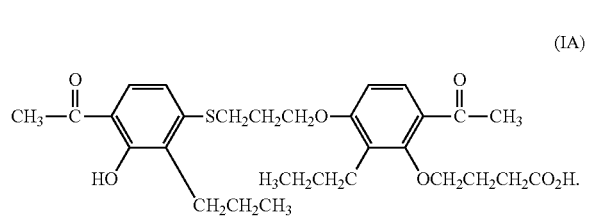

(IA)

3. The method of claim 2, in which the compound is present in an orthorhombic polymorphic form A that is substantially free of other polymorphic forms.

4. The method of claim 1, in which the compound is administered orally.

5. The method of claim 4, in which the compound is administered as a tablet or a capsule.

6. The method of claim 1, in which the compound is administered as a liquid dosage form.

7. The method of claim 1, in which the compound is administered in an amount from 100 to 4,000 mg/day, divided into one, two, or three portions.

8. A method of treating a patient suffering from non-alcoholic steatohepatitis (NASH) comprising administering to a patient in need thereof an effective amount of a compound of Formula (IB):

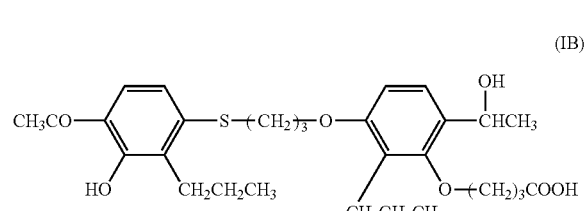

(IB)

or an ester thereof, or a pharmaceutically acceptable salt of each thereof.

9. A method of reducing liver inflammation in a patient suffering from non-alcoholic steatohepatitis (NASH) comprising administering to a patient in need thereof an effective amount of a compound of Formula (I):

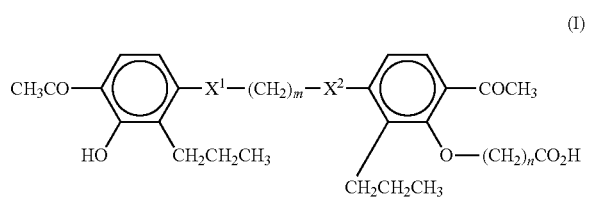

(I)

or an ester thereof, or a pharmaceutically acceptable salt of each thereof, wherein m is an integer from 2 to 5, and n is an integer from 3 to 8, $X^1$ and $X^2$ each independently represent a sulfur atom, oxygen atom, sulfinyl group or a sulfonyl group, provided that $X^1$ and $X^2$ are not simultaneously oxygen atom.

10. The method of claim 9, in which the compound of Formula (I) is of Formula (IA)

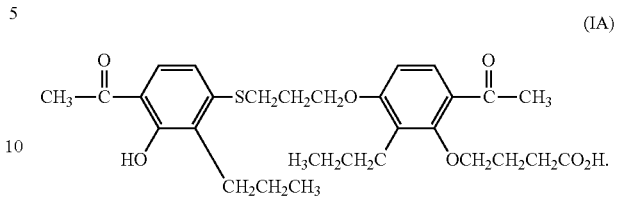

(IA)

11. The method of claim 10, in which the compound is present in an orthorhombic polymorphic form A that is substantially free of other polymorphic forms.

12. The method of claim 9, in which the compound is administered orally.

13. The method of claim 12, in which the compound is administered as a tablet or a capsule.

14. The method of claim 9, in which the compound is administered as a liquid dosage form.

15. The method of claim 9, in which the compound is administered in an amount from 100 to 4,000 mg/day, divided into one, two, or three portions.

16. A method of reducing liver inflammation in a patient suffering from non-alcoholic steatohepatitis (NASH) comprising administering to a patient in need thereof an effective amount of a compound of Formula (IB):

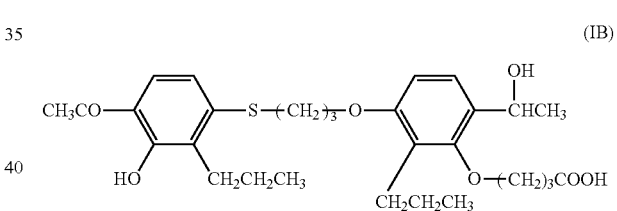

(IB)

or an ester thereof, or a pharmaceutically acceptable salt of each thereof.

17. A method of reducing hepatic fibrosis in a patient suffering from non-alcoholic steatohepatitis (NASH) comprising administering to a patient in need thereof an effective amount of a compound of Formula (I):

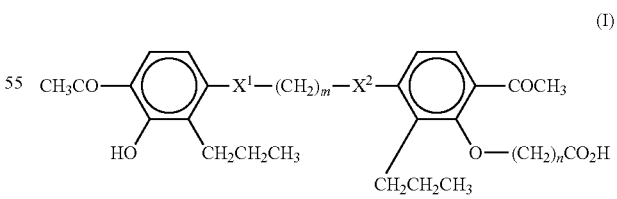

(I)

or an ester thereof, or a pharmaceutically acceptable salt of each thereof, wherein m is an integer from 2 to 5, and n is an integer from 3 to 8, $X^1$ and $X^2$ each independently represent a sulfur atom, oxygen atom, sulfinyl group or a sulfonyl group, provided that $X^1$ and $X^2$ are not simultaneously oxygen atom.

18. The method of claim 17, in which the compound of Formula (I) is of Formula (IA)

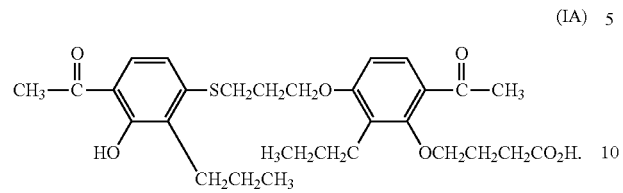

(IA)

19. The method of claim 18, in which the compound is present in an orthorhombic polymorphic form A that is substantially free of other polymorphic forms.

20. The method of claim 17, in which the compound is administered orally.

21. The method of claim 20, in which the compound is administered as a tablet or a capsule.

22. The method of claim 17, in which the compound is administered as a liquid dosage form.

23. The method of claim 17, in which the compound is administered in an amount from 100 to 4,000 mg/day, divided into one, two, or three portions.

24. A method of reducing hepatic fibrosis in a patient suffering from non-alcoholic steatohepatitis (NASH) comprising administering to a patient in need thereof an effective amount of a compound of Formula (IB):

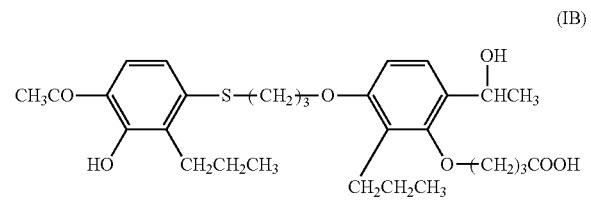

(IB)

or an ester thereof, or a pharmaceutically acceptable salt of each thereof.

25. A method of reducing damage to liver cells in a patient suffering from non-alcoholic steatohepatitis (NASH) comprising administering to a patient in need thereof an effective amount of a compound of Formula (I):

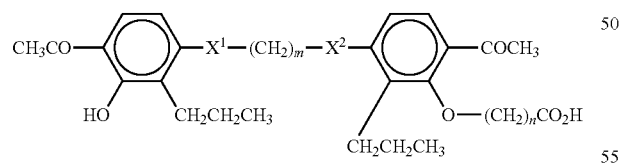

(I)

or an ester thereof, or a pharmaceutically acceptable salt of each thereof, wherein m is an integer from 2 to 5, and n is an integer from 3 to 8, $X^1$ and $X^2$ each independently represent a sulfur atom, oxygen atom, sulfinyl group or a sulfonyl group, provided that $X^1$ and $X^2$ are not simultaneously oxygen atom.

26. The method of claim 25, in which the compound of Formula (I) is of Formula (IA)

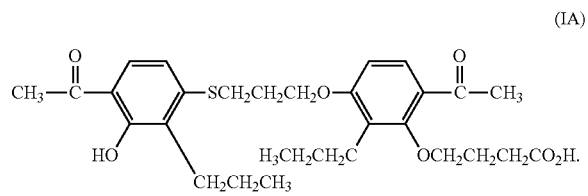

(IA)

27. The method of claim 26, in which the compound is present in an orthorhombic polymorphic form A that is substantially free of other polymorphic forms.

28. The method of claim 25, in which the compound is administered orally.

29. The method of claim 28, in which the compound is administered as a tablet or a capsule.

30. A method of reducing damage to liver cells in a patient suffering from non-alcoholic steatohepatitis (NASH) comprising administering to a patient in need thereof an effective amount of a compound of Formula (IB):

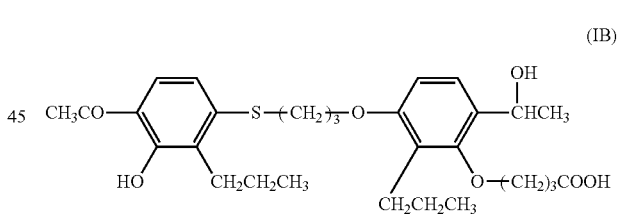

(IB)

or an ester thereof, or a pharmaceutically acceptable salt of each thereof.

* * * * *